United States Patent [19]

Pilgrim

[11] Patent Number: 5,376,672
[45] Date of Patent: Dec. 27, 1994

[54] METHOD FOR TREATING TENSION TYPE HEADACHES OR HEADACHES ASSOCIATED WITH DRUGS OR THEIR WITHDRAWAL

[75] Inventor: Alison J. Pilgrim, Greenford, Great Britain

[73] Assignee: Glaxo Group Limited, London, England

[21] Appl. No.: 30,387

[22] PCT Filed: Oct. 11, 1991

[86] PCT No.: PCT/GB91/01768

§ 371 Date: Apr. 6, 1993

§ 102(e) Date: Apr. 6, 1993

[87] PCT Pub. No.: WO92/06688

PCT Pub. Date: Apr. 30, 1992

[30] Foreign Application Priority Data

Oct. 12, 1990 [GB] United Kingdom ................ 9022250

[51] Int. Cl.$^5$ ............................................ A61K 31/405
[52] U.S. Cl. ...................................... 514/415; 514/929
[58] Field of Search ................................ 514/415, 929

[56] References Cited

U.S. PATENT DOCUMENTS

| | | | |
|---|---|---|---|
| 4,636,521 | 1/1987 | Coates | 514/415 |
| 4,816,470 | 3/1989 | Dowle et al. | 514/415 |
| 4,894,387 | 1/1990 | Butina et al. | 514/415 |
| 5,037,845 | 8/1991 | Oxford | 514/415 |

FOREIGN PATENT DOCUMENTS 2162522 2/1986 United Kingdom .

OTHER PUBLICATIONS

Buzzi et al., *Br. J. Pharmacol.*, 99, 1990, pp. 202–206.
Diener et al., *Headache*, 31(4), 1991, pp. 205–209.
Den Boer, *J. Neurol.*, suppl. 1, 238, 1991, pp. S28–S35.

*Primary Examiner*—Marianne M. Cintins
*Assistant Examiner*—K. Weddington
*Attorney, Agent, or Firm*—Bacon & Thomas

[57] ABSTRACT

The present invention provides a new medical use for 3-[2-(dimethylamino)-ethyl]-N-methyl-1H-indole-5-methanesulphonamide and physiologically acceptable salts and solvates thereof in the treatment of tension-type headache and headache associated with substances or their withdrawal.

12 Claims, No Drawings

METHOD FOR TREATING TENSION TYPE HEADACHES OR HEADACHES ASSOCIATED WITH DRUGS OR THEIR WITHDRAWAL

This invention relates to a new medical use for a certain indole derivative and pharmaceutical compositions containing it. In particular it relates to the use of 3-[2-(dimethylamino)-ethyl]-N-methyl-1H-indole-5-methanesulphonamide and physiologically acceptable salts and solvates thereof in treating certain types of headache.

3-[2-(dimethylamino)-ethyl]-N-methyl-1H-indole-5-methanesulphonamide, which may be represented by the formula

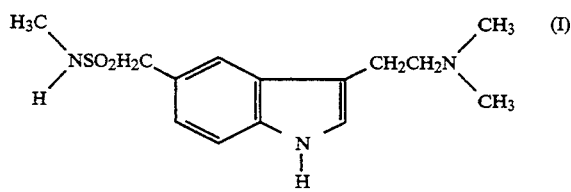

and its physiologically acceptable salts and solvates are disclosed in UK Patent Specification No. 2162522.

The compounds disclosed in the aforementioned patent specification are described as useful in treating and/or preventing pain resulting from dilatation of the cranial vasculature, in particular migraine and related disorders such as cluster headache.

We now find that the compound of formula (I) is also of use in the treatment of tension-type headache and headache associated with substances or their withdrawal. The exact mechanisms of tension-type headache are not known although involuntary tightening in muscles induced mentally or physically is important as are purely psychogenic mechanisms such as stress. Exposure to or withdrawal from certain substances is also known to cause headache. Drugs having a vasoconstrictor effect used in the treatment of migraine arc not generally applicable in the treatment of tension-type headache or headache associated with substances or their withdrawal, which are conventionally treated by administration of simple analgesics such as aspirin and paracetamol. Surprisingly, the compound of formula (I) is effective in the relief of such headaches.

According to one aspect of the invention we therefore provide the compound of formula (I)

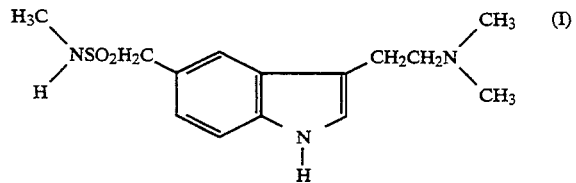

or a physiologically acceptable salt or solvate thereof for use in the treatment or prevention of tension-type headache or headache associated with substances or their withdrawal.

In an alternative or further aspect, the invention provides a method of treatment of a mammal, including man, suffering from or susceptible to tension-type headache or headache associated with substances or their withdrawal which comprises administering an effective amount of the compound of formula (I) or a physiologically acceptable salt or solvate thereof.

It will be appreciated that whilst the compound of formula (I) will primarily be of use in the alleviation of established symptoms, prophylaxis is not excluded.

In a further aspect, the invention provides the use of the compound of formula (I) or a physiologically acceptable salt or solvate thereof in the manufacture of a medicament for the treatment or prevention of tension-type headache or headache associated with substances or their withdrawal.

A further aspect of the invention provides pharmaceutical compositions for the treatment or prevention of tension-type headache or headache associated with substances or their withdrawal comprising as active ingredient a compound of formula (I) or a physiologically acceptable salt or solvate thereof.

Categories of headaches referred to herein are defined according to the classification and diagnostic criteria for headache disorders, cranial neuralgias and facial pain produced by the Headache Classification Committee of the International Headache Society, Cephalgia 1988, 8 suppl. 7:1-96.

The classification of tension-type headache embraces both chronic headaches (more than 15 days per month) and episodic headaches. Such headaches may be associated or unassociated with disorder of pericranial muscles.

The classification of headache associated with substances or their withdrawal embraces headache induced by acute or chronic substance use or exposure and headache associated with substance withdrawal after acute or chronic use. Headaches may be induced, for example, by the use of or exposure to substances such as alcohol, carbon monoxide, monosodium glutamate, analgesics and nitrates or nitrites. Headaches may also be induced by withdrawal from certain drugs, for example narcotics, alcohol, caffeine and ergotamine. Use of a compound of formula (I) or a physiologically acceptable salt or solvate thereof in the treatment of drug withdrawal headache, particularly ergotamine or analgesic withdrawal, is preferred.

Suitable physiologically acceptable salts of the compound of formula (I) include acid addition salts formed with organic or inorganic acids for example hydrochlorides, hydrobromides, sulphates, nitrates, phosphates, formates, mesylates, citrates, benzoates, fumarates, maleates and succinates.

In a particularly preferred embodiment of the present invention, the compound of formula (I) used is the succinate (1:1) salt.

The compound for use according to the invention may be administered as the raw chemical comprising the active ingredient compound in an amount of from 0.1 mg to 300 mg.

Conveniently, the compound for use according to the invention may be formulated in conventional manner using one or more pharmaceutically acceptable carders or excipients. Thus, the compound for use according to the invention may for example be formulated for oral, sub-lingual, buccal, parenteral, rectal or intranasal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such is binding agents (e.g.

pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For buccal administration the compositions may take the form of tablets or lozenges formulated in conventional manner.

The compound for use according to the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multi-dose containers, optionally with an added preservative.

The compositions for parenteral administration may take such forms as suspensions, solutions or emulsions in oily or aqueous vehicles, and may contain formulatory agents such as suspending, stabilizing and/or dispersing agents. Alternatively, the active ingredient may be in dry form such as a powder, crystalline or freeze-dried solid for constitution with a suitable vehicle, e.g. sterile pyrogen-free water or isotonic saline before use. They may be presented, for example, in sterile ampoules or vials.

The compound for use according to the invention may also be formulated in rectal compositions such as suppositories or retention enemas, e.g. containing conventional suppository bases such as cocoa butter or other glyceride.

Tablets for sub-lingual administration may be formulated in a conventional manner.

For intranasal administration the compound for use according to the invention may be used, for example, as a liquid in the form of, for example, a solution, suspension or emulsion, presented in the form of a spray or drops, or as a powder. Preferably the preparation for intra-nasal administration is delivered in the form of a spray or aerosol from an insufflator or from a pressurized pack or nebuliser with the use of a suitable propellant.

For administration by inhalation the compound for use according to the invention is conveniently delivered in the form of an aerosol spray presentation from presurized packs or a nebuliser, with the use of a suitable propellant, e.g. dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

It will be appreciated that the precise dose administered will depend on the age and condition of the patient and the frequency and route of administration and will be at the ultimate discretion of the attendant physician. The compound may be administered in single or divided doses and may be administered one or more times, for example 1 to 4 times per day.

A proposed dose of the active ingredient for use according to the invention for oral, sub-lingual, parenteral, buccal, rectal or intranasal administration to man (of approximately 70 kg bodyweight) for the treatment of tension-type headache or headache associated with substances or their withdrawal may be 0.1 to 300 mg of the active ingredient per unit dose which could be administered, for example, 1 to 4 times per day.

For oral administration a unit dose will preferably contain from 2 to 200 mg, more preferably 20 to 100 mg of the active ingredient. Dosages of the compound for use according to the invention for rectal or sub-lingual administration are similar to those for oral administration. A unit dose for parenteral administration will preferably contain 0.1 to 10 mg, more preferably 0.2 to 5 mg of the active ingredient.

For intranasal administration a unit dose may contain 1 to 100 mg, preferably 2 to 50 mg of the active ingredient.

Aerosol formulations are preferably arranged so that each metered dose or 'puff' delivered from a pressurized aerosol contains 0.2 mg to 2 mg of a compound for use according to the invention. Capsules and cartridges suitable for use in an insufflator or an inhaler may contain 0.2 mg to 20 mg of a compound of the invention. The overall daily dose by inhalation with an aerosol will be within the range 1 mg to 100 mg. Administration may be several times daily, for example from 2 to 8 times, giving for example 1, 2 or 3 doses each time.

The new use according to the present invention has been demonstrated in single center, double-blind, placebo-controlled, randomized, crossover studies.

In the first study, forty two patients, aged 18–65 years, who had experienced chronic tension-type headaches for at least one year and had a developing or established attack of chronic tension-type headache were recruited. Patients were excluded from the study if they had any other recurring headache disorders.

Patients received a 0.5 ml subcutaneous injection of isotonic saline (placebo) or of an isotonic solution containing 4mgml$^{-1}$ or 8mgml$^{-1}$ 3-[2-(dimethylamino)ethyl]-N-methyl-1H-indole-5-methanesulphonamide base as the succinate salt in a molar ratio of 1:1 (2 or 4 mg active ingredient) on three separate occasions separated by at least 72 hours, according to a randomization schedule. If symptom relief was inadequate two hours after taking the study medication, patients were offered rescue medication.

Pain relief was assessed at 10, 20, 30, 40, 60 and 120 minutes post-dosing using a six-point rating scale (Grades 1–6) and by patients completing visual analogue scale pain scores at pre-treatment and at the same post-treatment intervals (±5 cm).

31% and 28% of patients reported headache relief "much better" (grade 5) or "complete relief" (grade 6) 60 minutes post-dosing after 2 mg and 4 mg active ingredient respectively, compared with only 8% of patients after placebo. Patients also had significantly lower weighted mean visual analogue scale values over the first 120 minutes after dosing with 2 mg and 4 mg active ingredient (4.0 cm and 3.9 cm, $p=0.028$ and $p=0.009$ respectively).compared with placebo (4.5 cm). In addition a lower percentage of patients required rescue medication at 120 minutes after 2 mg and 4 mg active ingredient (15% and 13% respectively) compared with placebo (27%).

The results of this clinical trial clearly demonstrate the effectiveness of the compound of formula (I) or physiologically acceptable salts or solvates thereof for use in the treatment of tension-type headache.

In the second study, six patients, aged 18–65 years, who had been admitted to hospital for withdrawal from the chronic use of all analgesic or anti-migraine drugs, one of which was ergotamine, were recruited. Patients had a history of migraine but had further been diagnosed as having chronic headache associated with the chronic use of drugs (for more than six months).

Patients received a 0.5 ml subcutaneous injection of isotonic saline (placebo) or of an isotonic solution containing 8mgml$^{-1}$ 3-[2-(dimethylamino)-ethyl]-N-methyl-1H-indole-5-methanesulphonamide base as the succinate salt in a molar ratio of 1:1 (4 mg active ingredient) on separate occasions according to a randomization schedule.

The intensity of headache pain was assessed by the patients before treatment and up to 120 minutes after dosing.

In all six patients the severity of headache decreased rapidly after a single subcutaneous injection of the active ingredient (4 mg). No comparable decreases were seen when the same patients received placebo.

The results of this clinical trial demonstrate the effectiveness of the compound of formula (I) or physiologically acceptable salts or solvates thereof for use in the treatment of headache associated with substances or their withdrawal, particularly in the treatment of headache associated with drug withdrawal, for example ergotamine withdrawal.

I claim:

1. A method of treatment of treating a human suffering from a tension-type headache or headache associated with one or more drugs or their withdrawal which comprises administering a pharmaceutical composition comprising an effective amount of a compound of formula (I)

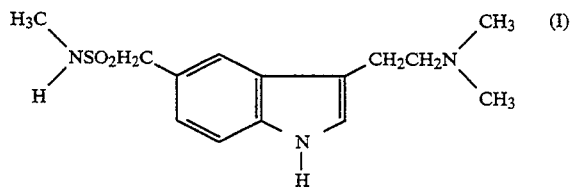

or a physiologically acceptable salt or solvate thereof together with one or more pharmaceutically acceptable carriers or excipients.

2. A method according to claim 1 wherein the pharmaceutical composition is adapted for oral administration.

3. A method according to claim 2 wherein the pharmaceutical composition contains a unit dose of 2 to 200 mg of the compound of formula (I) or a physiologically acceptable salt or solvate thereof.

4. A method according to claim 1 wherein the pharmaceutical composition is adapted for parenteral administration.

5. A method according to claim 1 wherein the pharmaceutical composition is adapted for intra-nasal administration.

6. A method according to claim 1 wherein the compound of formula (I) used is the succinate (1:1) salt.

7. A method of treating a human suffering from tension-type headache or headache associated with one or more drugs or their withdrawal which comprises administering an effective amount of a compound of formula (I)

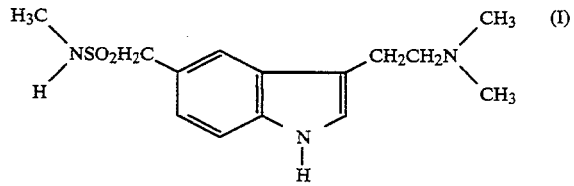

or a physiologically acceptable salt or solvate thereof.

8. A method according to claim 7 wherein the human is suffering from tension-type headache.

9. A method according to claim 8 wherein the human is not suffering from migraine.

10. A method according to claim 8 wherein the tension-type headache is chronic or episodic.

11. A method according to claim 7 wherein the human is suffering from headache associated with drug withdrawal.

12. A method according to claim 7 wherein the human is suffering from headache associated with ergotamine or analgesic withdrawal.

* * * * *